(12) United States Patent
Echner et al.

(10) Patent No.: US 9,437,340 B2
(45) Date of Patent: Sep. 6, 2016

(54) LEAF MODULE FOR A MULTI-LEAF COLLIMATOR AND MULTI-LEAF COLLIMATOR

(71) Applicants: Deutsches Krebsforschungszentrum, Heidelberg (DE); Precisis AG, Heidelberg (DE)

(72) Inventors: Gernot Echner, Wiesenbach (DE); Armin Runz, Neckargemünd (DE); Martin Baumann, Östringen (DE); Stefan Ueltzhöffer, Schwetzingen (DE)

(73) Assignees: DEUTSCHES KREBSFORSCHUNGSZENTRUM, Heidelberg (DE); PRECISIS AG, Heidelberg (DE)

( * ) Notice: Subject to any disclaimer, the term of this patent is extended or adjusted under 35 U.S.C. 154(b) by 0 days.

(21) Appl. No.: 14/415,097

(22) PCT Filed: Jul. 18, 2013

(86) PCT No.: PCT/EP2013/065176
§ 371 (c)(1),
(2) Date: Jan. 15, 2015

(87) PCT Pub. No.: WO2014/013013
PCT Pub. Date: Jan. 23, 2014

(65) Prior Publication Data
US 2015/0170778 A1     Jun. 18, 2015

(30) Foreign Application Priority Data

Jul. 19, 2012   (EP) .................................... 12177138

(51) Int. Cl.
*G21K 5/04*      (2006.01)
*G21K 1/04*      (2006.01)
*A61N 5/10*      (2006.01)

(52) U.S. Cl.
CPC ............. *G21K 1/046* (2013.01); *A61N 5/1045* (2013.01)

(58) Field of Classification Search
USPC ........... 250/396 R, 397, 492.1, 492.3, 505.1, 250/515.1
See application file for complete search history.

(56) References Cited

U.S. PATENT DOCUMENTS 4,794,629 A     12/1988  Pastyr et al.
5,351,280 A *    9/1994  Swerdloff et al. .............. 378/65
(Continued)

FOREIGN PATENT DOCUMENTS

WO     WO 2008/140458 A1     11/2008

OTHER PUBLICATIONS

Webb et al., "A New Concept of Multileaf Collimator (the Shuttling Mlc) an Intepreter for High-Efficiency IMRT," *Phys. Med. Biol.* 45, pp. 3343-3358 (2000).
International Search Report issued in related International Patent Application No. PCT/EP2013/065176, completed Aug. 7, 2013.
Office Action issued in related U.S. Appl. No. 14/415,086, dated Sep. 29, 2015.

(Continued)

*Primary Examiner* — Nicole Ippolito
(74) *Attorney, Agent, or Firm* — Foley & Lardner LLP

(57) ABSTRACT

The invention relates to a leaf module (102) for a multi-leaf collimator (132), comprising a leaf unit (104) and a leaf drive unit (106), wherein the leaf unit (104) comprises a leaf (108) for shielding beams from a selected area, and the leaf unit (104) is mounted displaceably in an adjusting direction (110), wherein the leaf drive unit (106) is designed to displace the leaf unit (104) linearly in the adjusting direction (110), and wherein the leaf drive unit (106) comprises at least one drive mechanism (112), being designed in such a way that the drive mechanism (112) operates based on pneumatic actuation. Furthermore, the invention relates to a multi-leaf collimator (132) comprising a plurality of leaf modules (102) according to the invention. The invention is based on the objective of designing a leaf module (102) and a multi-leaf collimator (132) as compactly as possible, while achieving a simple, reliable and variable adjustability of the leaf unit (104). The invention is regarded to be particularly suitable for implementation in Cobalt-60 or mid- to low-end linac radiotherapy apparatuses.

18 Claims, 4 Drawing Sheets

(56) References Cited

U.S. PATENT DOCUMENTS

Figure 1:
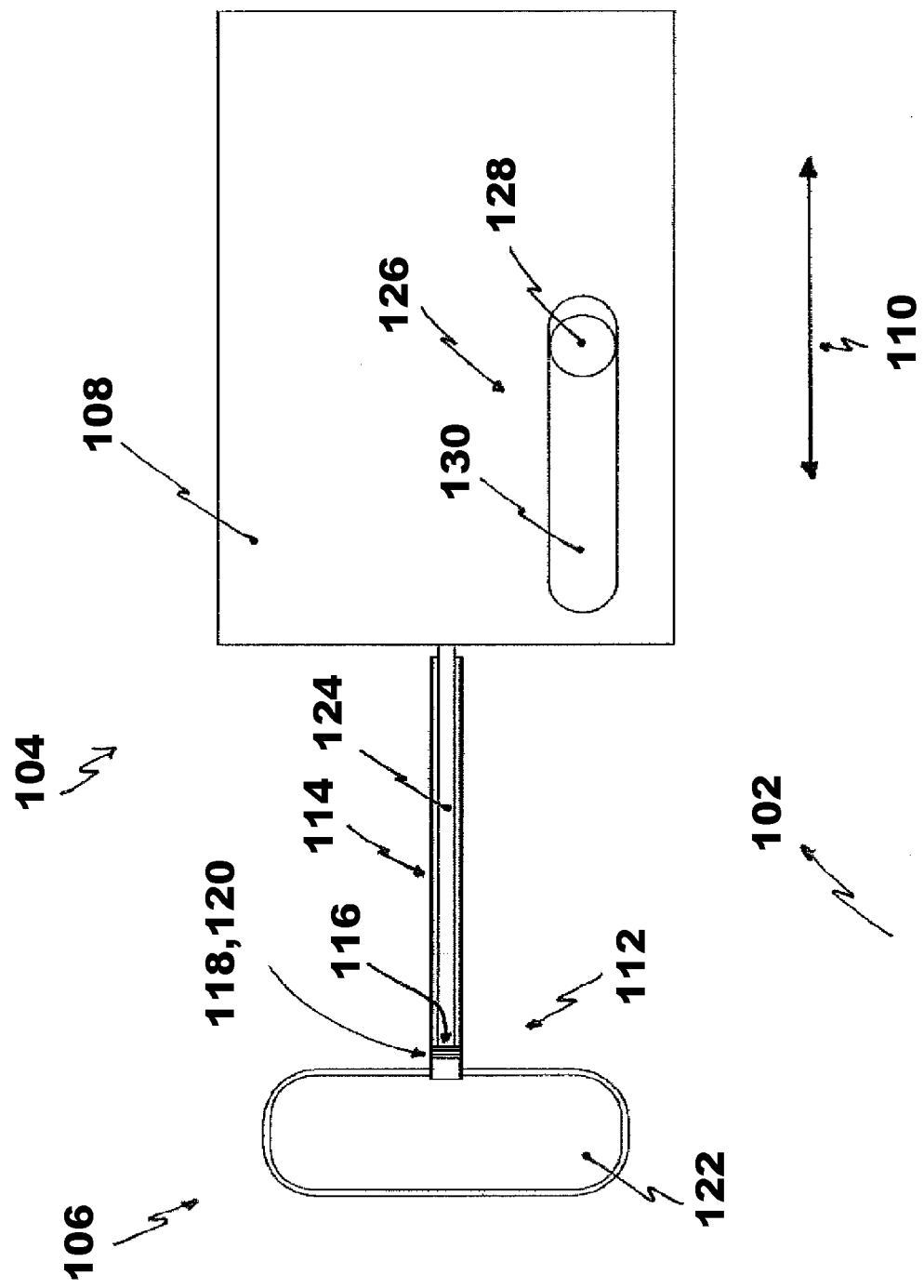

| | | | |
|---|---|---|---|
| 5,668,371 A * | 9/1997 | Deasy et al. ...................... 850/1 |
| 2007/0164239 A1 * | 7/2007 | Terwilliger ............ G21K 1/046 |
| | | | 250/505.1 |
| 2009/0041199 A1 | 2/2009 | Bohn |
| 2009/0207975 A1 | 8/2009 | Bourne |

OTHER PUBLICATIONS

Office Action issued in related U.S. Appl. No. 14/415,086, dated Jan. 21, 2016.

Notice of Allowance issued in related U.S. Appl. No. 14/415,086, dated May 6, 2016.

* cited by examiner

LEAF MODULE FOR A MULTI-LEAF COLLIMATOR AND MULTI-LEAF COLLIMATOR

The invention relates to a leaf module for a multi-leaf collimator, comprising a leaf unit and a leaf drive unit, wherein the leaf unit comprises a leaf for shielding beams from a selected area, and the leaf unit is mounted displaceably in an adjusting direction, wherein the leaf drive unit is designed to displace the leaf unit linearly in the adjusting direction, and wherein the leaf drive unit comprises at least one drive mechanism. Additionally, the invention relates to a multi-leaf collimator.

Various embodiments of multi-leaf collimators comprising leaf modules each featuring a leaf unit and a leaf drive unit are known in the art. Multi-leaf collimators of such kind are preferably employed for controlling a shape of a high-energy radiation beam emanating from a radiation source and propagating in a direction of propagation.

Multi-leaf collimators are commonly used in treatment devices for oncological radiation therapy. Said collimators delimit high-energy beams, such as high energy radiation of a Cobalt-60 (Co-60) radiotherapy apparatus or a linear accelerator (linac), in such a way that the beams have exactly the same shape as the treatment object. Since such irradiation, e.g. of a tumor, occurs from various directions, it is possible to achieve a great irradiation intensity of the tumor and, at the same time, to stress the surrounding tissue only to a limited extent.

The leaves of the multi-leaf collimator may also be called "shutter blades" or "lamellae". The multi-leaf collimators may also be called contour collimators since due to the positioning of the leaves, contours of treatment objects, for example tumors, can be recreated for each beam application, each of which occurs from a certain solid angle. This is important in order to protect the adjacent healthy tissue to the greatest extent possible. In the case of organs at risk, such as spine or nerves, this is particularly necessary in order to preserve their functional capability.

A general example of a multi-leaf collimator comprising leaf modules with a leaf unit and a leaf drive unit is obtainable from U.S. Pat. No. 4,794,629. In such multi-leaf collimators, each leaf unit must be moved into a certain position. Thus, in most cases, a leaf drive unit must be assigned to each leaf unit. According to the aforementioned publication, no separate motor is assigned to each leaf unit, which is why the leaf units are arranged in series by means of drive couplings and locking devices. However, it has also been known to assign an electric motor to each leaf unit that positions the leaf unit via a pinion and a gear rod-like drive engagement. As a matter of course, although yielding reliable and exact results, such collimator designs are complicated and costly.

Several proposals have also been made to employ drive mechanisms operating based on piezoelectric actuation within leaf drive units of leaf modules, e.g. according to printed publication US 2009/0041199 A1. This printed publication generally discloses a leaf module for a multi-leaf collimator and a multi-leaf collimator of the kind mentioned at the beginning of this specification. However, again, such devices are predominantly designed for up-to-date linac radiotherapy machines, being extremely costly, complicated and subject to regular and specialized maintenance.

Despite some undisputed technological and practical advantages of modern linacs over Co-60 radiotherapy machines, the latter still occupy an important place in radiotherapy, mainly because of the considerably lower capital, installation and maintenance costs of Co-60 machines compared with said linacs. In the developing world, Co-60 machines, because of their relatively lower costs, simplicity of design and ease of operation, are likely to play an important role in cancer therapy for the foreseeable future. Summarizing, besides sophisticated and costly designs as outlined above, a demand also exists for leaf modules and multi-leaf collimators of the kind mentioned at the beginning of this specification, however being suitable for mid- and low-end radiotherapy machines, be it Co-60, linac, or the like.

For such machines, manually adjustable leaf modules and multi-leaf collimators are known. Particularly for small collimators (e.g. micro-multi-leaf collimators) and mid-size collimators rather simple technical solutions have been proposed, wherein the leaves may be adjusted manually or supported by a suitable spring force. Commonly, in order to predetermine a desired shape of the irradiation beam, or, with other words, to select the area to be shielded from beams, a template may be inserted into the collimator. Then, manually and/or based on said spring force, each leaf will be displaced in the adjusting direction and directed towards the radiation source until it abuts the template with its front end. Subsequently, the leaf may be locked in place, and the template may be removed. In an alternative, the template may remain in place if it does not interfere with the radiation, e.g. if it is made of a suitable material such as PMMA, and a suitable spring force will be at disposal to keep the template in its place. In yet a further alternative, the template may be kept in place by screws, pins, or the like, for instance in micro-multi-leaf collimators.

However, leaf modules and multi-leaf collimators known in the art and as outlined above also exhibit serious drawbacks.

During an irradiation treatment, the irradiation head usually has to be moved into various but defined angles with respect to the target volume, e.g. the tumor. Thus, it is desirable to design such a collimator as compact and lightweight as possible. In each new position, the collimator has to be readjusted to comply with the updated radiation beam shape needed in the new position. It is however obvious that in gantry positions differing from the initial position (which is the 0° gantry position), a manual displacement of individual leaves is hardly or not possible due to limited accessibility of the drive unit and/or the weight of the leaves. Thus, manually operable collimators may usually merely be adjusted in the 0° gantry position. This leads to an unsatisfactory variability of the adjustability of the collimator, substantially prolonging and complicating the irradiation treatment.

As outlined above, leaf drive units may comprise a spring to promote adjusting of the leaf towards the radiation source. Usually, for such purpose, tension or compression springs are employed, acting upon the leaves via a suitable redirection of the spring force. However, if the gantry is out of the 0° position, the springs will be too weak to displace the leaves due to the added leaf weight being effective in the adjusting direction, and the opposite side springs will be to strong, displacing the leaves with too much force. Hence, again, such collimators may usually merely be adjusted in the 0° gantry position.

Additionally, when applying tension or compression springs in the leaf drive unit, a steep load deflection curve (i.e. steep spring characteristics) must be regarded as being unfavorable due to highly varying spring forces when adjusting the leaves. Thus, very long and considerably pre-loaded springs will have to be employed. However, such springs will result in an unwanted enlargement of the collimator. Consequently, due to the increased scale of the irradiation head, the clearance between the irradiation head and the patient will have to be enlarged, diminishing the desired impact of radiation and even preventing the irradiating in certain gantry positions altogether.

The invention is therefore based on the objective of relieving at least one of the drawbacks as outlined above.

The invention is additionally based on the objective of designing a leaf module for a multi-leaf collimator and a multi-leaf collimator of the kind mentioned at the beginning, respectively, in such a way that with a design of the leaf module being as compact as possible, a simple, reliable and variable adjustability of the leaf unit is achieved.

This objective is attained in accordance with the invention by the subject-matter disclosed in the independent claims. Preferred embodiments which may be realized in an isolated way or in combination with other preferred embodiments are disclosed subsequently and in the dependent claims.

Thus, in a first major aspect of the present invention, a leaf module for a multi-leaf collimator of the kind mentioned at the beginning is designed in such a way that the drive mechanism operates based on pneumatic actuation.

According thereto, the drive mechanism is adapted to employ pressurized gas, in particular air, in order to displace the leaf in the adjusting direction, in particular being directed towards the radiation source or a suitable template which defines the desired beam shape. This may for instance be achieved by an air spring, pneumatic spring or air suspension being comprised by the drive mechanism. The drive mechanism according to the invention may achieve maximum compactness, in particular when being compared to common springs as discussed above. For instance, air springs or the like may at least partly be integrated with the leaf unit, reducing the overall length of the collimator as seen in the adjusting direction.

The drive mechanism according to this proposal will do away with the need for manual adjusting of the leaves. Also, no long and considerably preloaded springs will be needed within the drive mechanism, also getting rid of means for a suitable redirection of the spring force which are otherwise needed at least when using tension springs.

Thus, a compact and simple design of the leaf unit may be attained, permitting a minimum clearance between the irradiation head and the patient.

Also, the drive mechanism operating based on pneumatic actuation will allow for an adjustability of the leaves in any desired gantry position differing from the initial 0° position.

For any gantry position, a gas pressure being sufficient but not too large to adjust the leaf may be supplied to the drive mechanism, clearly outperforming the potential of manual or common (tension) spring adjusting.

Additionally, the drive mechanism operating based on pneumatic actuation may be designed to exhibit any desired load deflection curve (i.e. spring characteristics) when adjusting the leaf. Preferably, a flat load deflection curve may be achieved by appropriately configuring the drive mechanism, without having to enlarge the size of the mechanism to an unfavorable extent compared to a solution based on common (tension) springs.

The term "leaf unit" as used herein generally relates to a unit comprising a leaf. Therefore, in general, it is not necessarily required that the leaf unit comprises any other component apart from the leaf. However, without departing from the inventive idea, a leaf unit according to the term used herein may just as well comprise other parts aside from the leaf, as will be described below in detail.

The term "leaf drive unit" as used herein generally relates to a unit comprising at least one drive mechanism adapted to displace the leaf in the adjusting direction. The leaf drive unit may comprise one or more drive mechanisms, for example one drive mechanism adapted to displace the leaf towards the radiation beam (or the template, if applicable), and one drive mechanism to retract the leaf from the radiation beam (e.g. in order to allow the insertion of a different template). The unit may comprise further means, such as means for mounting the leaf in the adjusting direction. It is not necessary, however, that the leaf drive unit should generally be distinguishable from the drive mechanism. For instance, in case a leaf drive unit comprises a single drive mechanism, the drive mechanism might be regarded as being configured integrally with the leaf drive unit. In such a case, no tangible difference might be detectable by a person skilled in the art between the leaf chive unit and the drive mechanism.

The term "drive mechanism" as used herein relates to means adapted to displace the leaf in the adjusting direction. Said means may be adapted to displace the leaf in only one or in both orientations or ways (i.e. forwards and/or backwards) within the adjusting direction. The term "drive mechanism" itself is not restricted to a specific mode of operation, in fact a drive mechanism according to the term used herein may generally be designed to operate in any thinkable way, such as manually, motor- or electrically driven, or according to the invention as outlined above, or the like.

In a first optional and preferred embodiment of the leaf module according to the invention, the drive mechanism comprises a pressure cylinder. The pressure cylinder is well suited to transfer a gas pressure being generated or being available in the leaf drive unit to the leaf unit, in particular by transforming said gas pressure into a displacing movement of the leaf or the entire leaf unit. Within the pressure cylinder, a gas pressure may act upon a member being assigned to the leaf drive unit, or, in an alternative, it may as well act upon a member being assigned to the leaf unit, without departing from the inventive idea.

According to another particularly preferred embodiment, the drive mechanism comprises a reservoir for compressed gas, in particular wherein the reservoir communicates with a pressure cylinder being comprised by the drive mechanism. Said optional pressure cylinder has already been referred to above. With a reservoir for compressed gas being comprised by the drive mechanism, a remarkable variability of the adjusting of the multi-leaf collimator may be achieved. Accordingly, compressed gas may be available in any gantry position, in particular any position differing from the 0° initial position. No pressure line, electrical connection to a pressure pump, or the like will be needed to be connected to the drive mechanism when carrying out a treatment cycle. The reservoir for compressed gas may be adapted to be charged by a hand or foot pump, being particularly suited for mid- or low-end radiotherapy machines, possibly being run in remote areas. When configuring the capacity of an optional reservoir for compressed gas, the deflection curve (i.e. the spring characteristics) of the drive mechanism operating based on pneumatic actuation may be freely determined. It is preferred that the capacity, i.e. the size of said reservoir be large compared to the volume of an optional pressure cylinder as outlined above. Thus, a particularly preferred flat load deflection curve of the drive mechanism may be attained. Referring to the fraction of the capacity (volume) of said reservoir and the combined volume of all optional pressure cylinders being supplied by one reservoir, a number of between 5 and 10 is particularly preferred.

In addition or alternatively, according to another particularly preferred embodiment, the drive mechanism comprises a piston, wherein the piston is linked directly or indirectly to the leaf unit, and wherein a displacement of the piston results in a displacement of the leaf unit. Said piston is particularly suited to interact with an optional pressure cylinder being comprised by the drive mechanism, as outlined above. Thus, in a further embodiment, the drive mechanism comprises both a pressure cylinder as outlined above and a piston which is displaceably arranged in the adjusting direction within the pressure cylinder, transforming the pressure applied to the cylinder into a displacing movement of the leaf or the entire leaf unit. Here, such a piston is defined as forming a part of the drive mechanism due to the above generation of a displacing movement. Nevertheless, a person skilled in the art could as well regard such a piston being linked directly or indirectly to the leaf unit as forming a part of the leaf unit, however without departing from the underlying inventive idea.

An optional piston as outlined above may comprise a sealing element, in particular an o-ring. Said sealing element proves to be particularly beneficial in case the piston is adapted to be arranged in a pressure cylinder as outlined above.

In an optional further embodiment of the leaf module according to the invention, the leaf unit comprises a guiding rod extending in the adjusting direction, wherein the guiding rod is a separate part being attached to the leaf, or wherein the guiding rod is an integral part of the leaf, in particular wherein the guiding rod is linked to a piston being comprised by the drive mechanism. Said optional piston has been outlined above in detail. Employing a guiding rod as proposed here yields several benefits. First of all, the leaf which normally comprises heavy and expensive material may be of smaller length, as the guiding rod will provide sufficient range for the displacement of the leaf unit. Consequently, the entire leaf module may be constructed lighter and more compact. Additionally, for the displacing and adjusting of the leaf unit, a defined interaction of the leaf drive unit with the guiding rod instead of the much larger leaf may be envisaged, yielding a substantial advantage with regards to the precision of adjustment.

Further optionally, related to embodiments with a leaf unit comprising a guiding rod being separately attached to the leaf, the guiding rod may be attached to the leaf by form-fitting and/or force-locking, in particular wherein the guiding rod may be inserted into a channel located on the surface of the leaf, wherein the channel represents a negative pattern of the shape of the guiding rod. According to this embodiment, the guiding rod is safely and easily attachable to the leaf, nevertheless without enlarging the thickness of the leaf unit and thus retaining the compactness of the leaf unit and the entire leaf module. Hence, it will be preferred that the outer surface of the guiding rod and the surrounding surface of the leaf are arranged in one single joint plane.

Further, related to embodiments with a leaf unit comprising a guiding rod, in another optional embodiment the guiding rod is displaceably arranged in a pressure cylinder being comprised by the drive mechanism, in particular wherein the pressure cylinder provides a linear guidance to the guiding rod. Details of said optional pressure cylinder have already been outlined above.

According to a more general optional embodiment, the leaf drive unit is designed to displace the leaf unit in the adjusting direction and additionally provide guidance to the leaf unit with respect to any direction being oriented perpendicularly related to the adjusting direction. By combining the tasks to displace the leaf unit in the adjusting direction and additionally provide aforesaid guidance to the leaf within the leaf drive unit, a leaf module with compact design providing very precise and stable adjustability of the leaf unit may be obtained.

The term "guidance" as used herein refers to a technical effect achieved by appropriate means which properly impedes the leaf unit from deviating from the axis represented by the adjusting direction by a non-tolerable value. In the above optional embodiments referring to said guidance, further guiding or guide elements assigned to the leaf unit and not comprised by the leaf drive unit may be constructed less complex compared to the known art or may even become unnecessary.

According to another preferred embodiment of the leaf module according to the invention, the leaf drive unit comprises further drive mechanisms. In total, the leaf drive unit may not only comprise one, but may optionally comprise two or more drive mechanisms, if appropriate. A preferred embodiment comprises a drive mechanism operated based on pneumatic actuation according to the invention to displace the leaf forwards within the adjusting direction, i.e. towards the radiation beam or the template, if applicable. Additionally, in this embodiment, the leaf drive unit comprises a second drive mechanism in order to retract the leaf from the beam or the template, if applicable. With other words, said optional second drive mechanism is adapted to displace the leaf backwards within the adjusting direction. It is noted that the term "second drive mechanism" as used herein refers to an optional mechanism to retract the leaf which, compared to the drive mechanism as outlined in the preceding parts of this specification, does not necessarily, but may operate based on pneumatic actuation.

In a further embodiment of the leaf module, the leaf material comprises a high density material, in particular brass, lead or tungsten. Tungsten has been found to have the capacity to very effectively shield beams from selected areas and is widely used in modern linac apparatuses. However, it is noted that brass leaf material may be obtained at approximately ¹⁄₆₀ of the price for tungsten. Due to the impaired shielding capacity of brass compared with tungsten, however, brazen leaves will usually have to exhibit approx. twice the height of comparable tungsten leaves. Nonetheless, brazen leaves may be preferred in particular for mid- to low-end multi-leaf collimators and radiotherapy machines, respectively. Generally, any material, in particular high density material, which has the capacity to shield beams, may be employed as leaf material in order to implement the invention.

In a second major aspect of the invention, a multi-leaf collimator is disclosed, wherein the multi-leaf collimator comprises a plurality of leaf modules according to the invention. Relating to the essence and features of the multi-leaf collimator according to the invention, reference is at first made to all previous paragraphs of this specification. In other words, the essence and benefits of the multi-leaf collimator according to the invention will already become manifest from the previous paragraphs describing aspects of the leaf module. Also, it is obvious that within the multi-leaf collimator according to the invention, any embodiment or any combination of aspects of the leaf module according to the invention as specified in the previous parts of this specification may be employed. When being employed within the multi-leaf collimator according to the invention, it is understood that the leaf module according to the invention and/or further aspects of the leaf module according to the optional embodiments as explained above, also aspects being combined, will yield the advantageous effects as described above also with relation to the multi-leaf collimator.

In a first further optional embodiment of the multi-leaf collimator according to the invention, the multi-leaf collimator is adapted for application in a Cobalt-60 radiotherapy apparatus. The persistent significance of said Co-60 radiotherapy machines for radiation therapy has been outlined above. The underlying invention is regarded to be particularly suitable for being employed in Co-60 radiotherapy machines or in mid- and low-end linac apparatuses, but is not restricted thereto. Corresponding advantageous effects of the invention regarding such applications have already been outlined, and full reference is made to these explanations. With the underlying invention, a leaf module and thus also a multi-leaf collimator being as compact as possible may be designed, wherein a simple, reliable and variable adjustability of the leaf unit is achievable. Said benefits do particularly well match the requirement profile for Co-60 and/or mid- to low-end linac machines, in particular if radiotherapy has to be provided in remote regions and/or with insufficiently qualified medical and maintenance staff and/or with limited financial resources. In particular, according to the invention, a multi-leaf collimator may be provided which operates being independent of a power network.

In yet a further embodiment of the multi-leaf collimator according to the invention, two assemblies of leaf modules are provided, wherein each assembly comprises a plurality of leaf modules according to the invention, and wherein the leaf modules of each assembly face each other. Consequently, by adjusting the leaf units facing each other in their respective adjusting direction, an area of arbitrary shape, in particular any contour of a treatment object, for example a tumor, can be recreated for beam application.

Summarizing, the following embodiments are preferred embodiments of the present invention:

EMBODIMENT 1

A leaf module for a multi-leaf collimator comprising a leaf unit and a leaf drive unit, wherein the leaf unit comprises a leaf for shielding beams from a selected area, and the leaf unit is mounted displaceably in an adjusting direction, wherein the leaf drive unit is designed to displace the leaf unit linearly in the adjusting direction, and wherein the leaf drive unit comprises at least one drive mechanism, characterized in that the drive mechanism operates based on pneumatic actuation.

EMBODIMENT 2

The leaf module according to the preceding embodiment, characterized in that the drive mechanism comprises a pressure cylinder.

EMBODIMENT 3

The leaf module according to any one of the preceding embodiments, characterized in that the drive mechanism comprises a reservoir for compressed gas, in particular wherein the reservoir communicates with a pressure cylinder being comprised by the drive mechanism.

EMBODIMENT 4

The leaf module according to any one of the preceding embodiments, characterized in that the drive mechanism comprises a piston, wherein the piston is linked directly or indirectly to the leaf unit, and wherein a displacement of the piston results in a displacement of the leaf unit.

EMBODIMENT 5

The leaf module according to the preceding embodiment, characterized in that the piston comprises a sealing element, in particular an o-ring.

EMBODIMENT 6

The leaf module according to any one of the preceding embodiments, characterized in that the leaf unit comprises a guiding rod extending in the adjusting direction, wherein the guiding rod is a separate part being attached to the leaf, or wherein the guiding rod is an integral part of the leaf, in particular wherein the guiding rod is linked to a piston being comprised by the drive mechanism.

EMBODIMENT 7

The leaf module according to the preceding embodiment, characterized in that the guiding rod is displaceably arranged in a pressure cylinder being comprised by the drive mechanism, in particular wherein the pressure cylinder provides a linear guidance to the guiding rod.

EMBODIMENT 8

The leaf module according to any one of the preceding embodiments, characterized in that the leaf drive unit is designed to displace the leaf unit in the adjusting direction and additionally provide guidance to the leaf unit with respect to any direction being oriented perpendicularly related to the adjusting direction.

EMBODIMENT 9

The leaf module according to any one of the preceding embodiments, characterized in that the leaf comprises a high density material, in particular brass, lead or tungsten.

EMBODIMENT 10

A multi-leaf collimator, characterized by a plurality of leaf modules according to any one of the preceding embodiments.

EMBODIMENT 11

The multi-leaf collimator according to the preceding embodiment, characterized in that the multi-leaf collimator is adapted for application in a Cobalt-60 radiotherapy apparatus.

EMBODIMENT 12

The multi-leaf collimator according to any one of the two preceding embodiments, characterized by two assemblies of leaf modules, wherein each assembly comprises a plurality of leaf modules according to any one of embodiments 1 to 9, and wherein the leaf modules of each assembly face each other.

In the following, the invention will further be explained by way of both schematic and exemplary drawings. In the figures, identical reference numbers refer to identical components or components having the same or similar functions. Thus, such components and referring reference numbers might not be repeatedly explained with regard to each figure, and explanations given on the occasion of preceding figures are referred to in such cases. In the figures, aspects of the leaf module and also aspects of the multi-leaf collimator according to the invention will be explained referring to preferred embodiments. While explaining aspects of the leaf module according to the invention, reference will also be made to aspects of the multi-leaf collimator according to the invention. The exemplary embodiments related to in the figures and the referring explanations are merely given for illustrative purposes, and the invention is not restricted to these embodiments.

Shown are in

Figure 2:
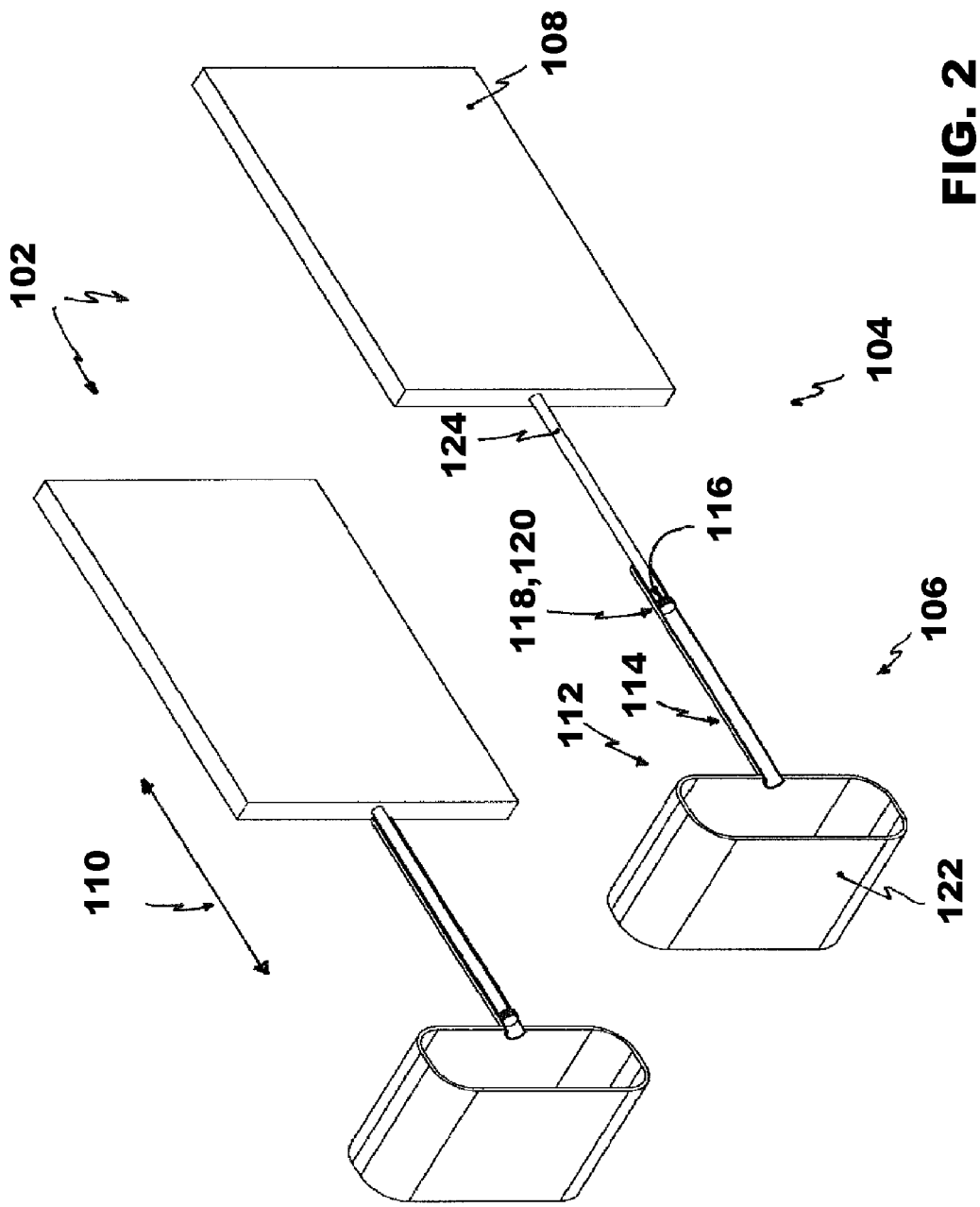
Figure 3:
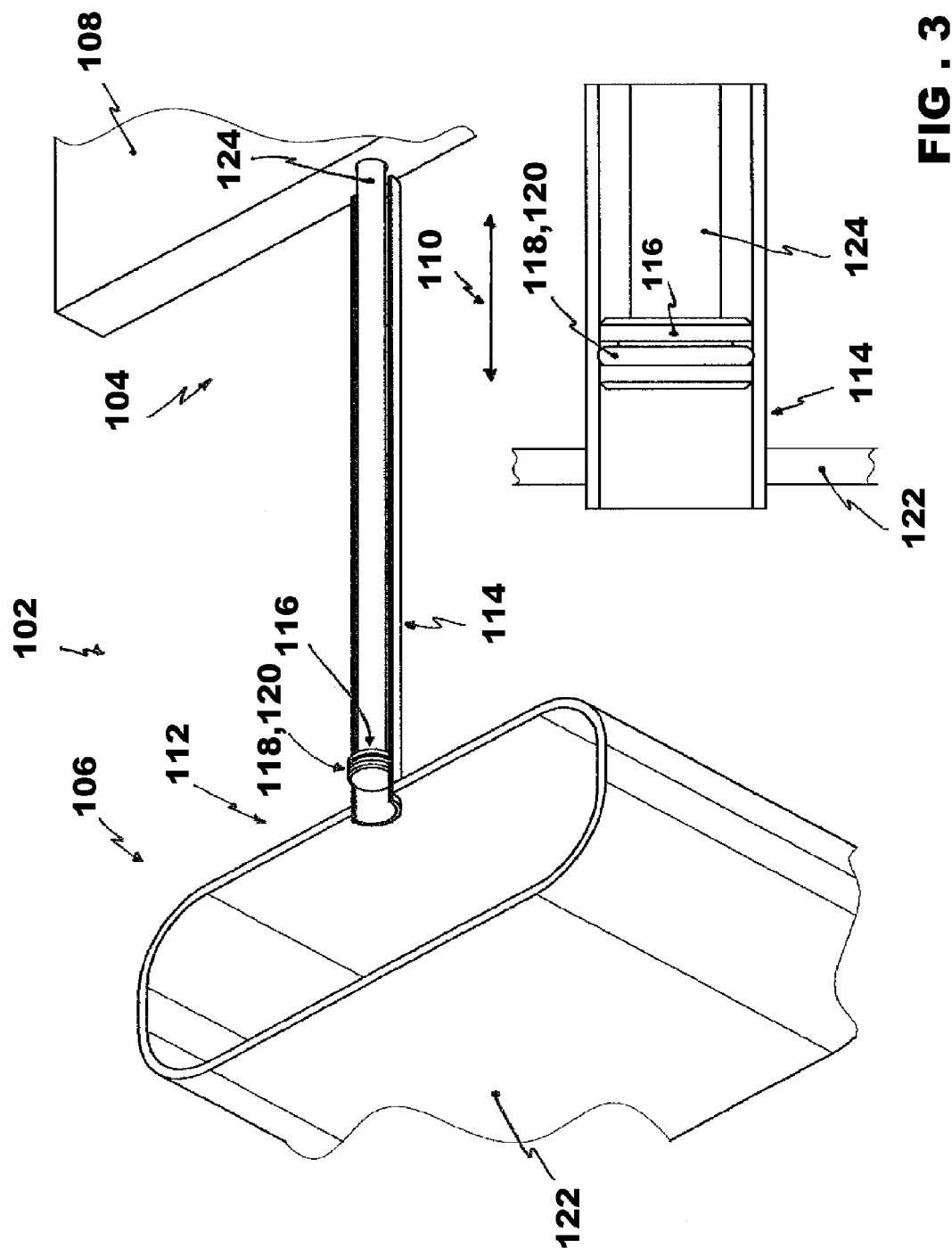
Figure 4:
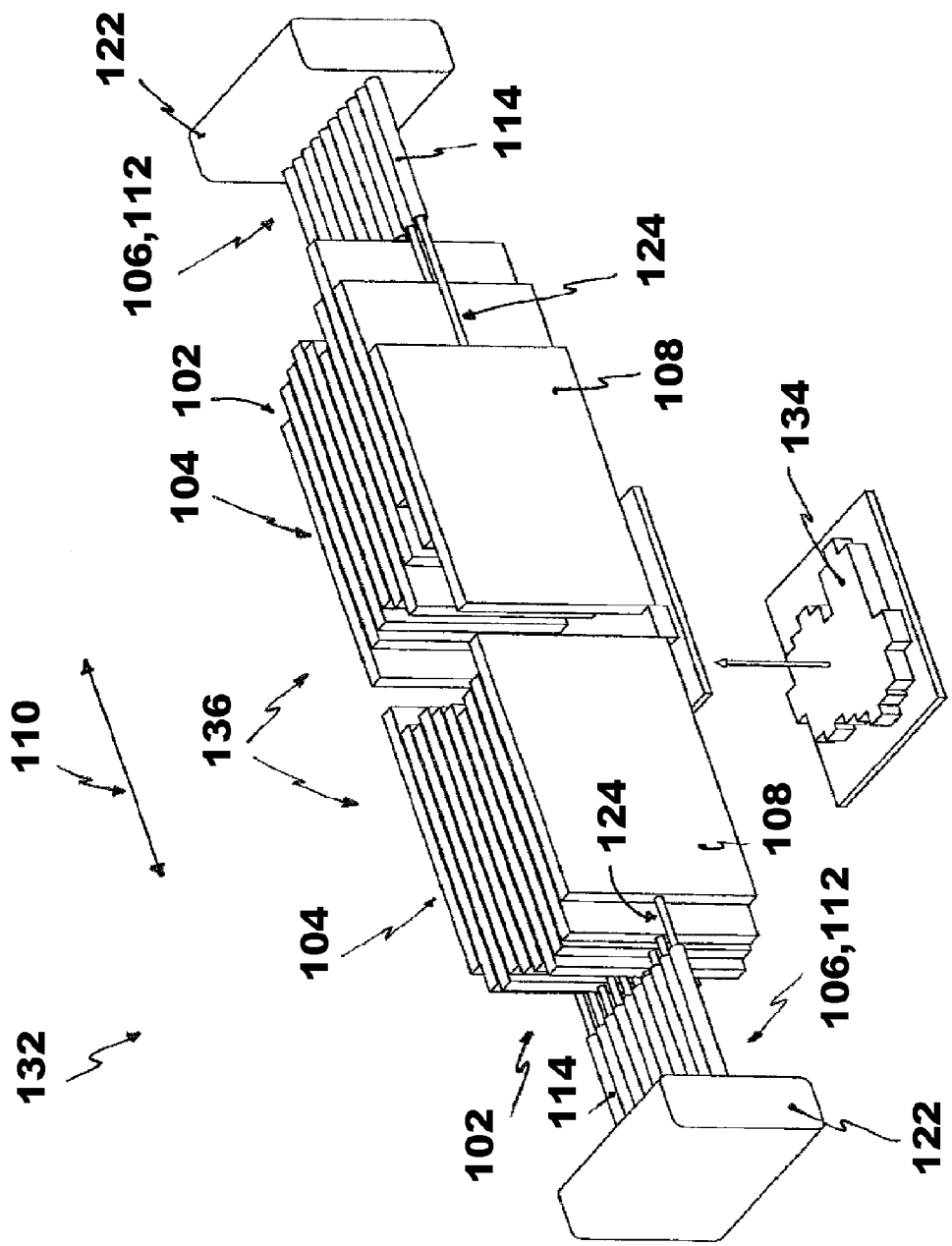

FIG. 1 in a predominantly schematic side view a first exemplary embodiment of the leaf module according to the invention, FIG. 2 in a predominantly schematic perspective view a second exemplary embodiment of a leaf module according to the invention, shown with both retracted and extended leaf unit, FIG. 3 two views of details pertaining to both embodiments according to FIGS. 1 and 2, and FIG. 4 in a predominantly schematic perspective view an exemplary embodiment of the multi-leaf collimator according to the invention, illustrating the insertion of a template and the adjusting of the collimator.

FIG. 1 discloses in a predominantly schematic side and partly sectional view a first exemplary embodiment of the leaf module 102 according to the invention. The leaf module 102 comprises a leaf unit 104 and a leaf drive unit 106, wherein the leaf unit 104 comprises a leaf 108 for shielding beams from a selected area. The beams will usually be emitted from a radiation source (not shown) which is arranged above the leaf module 102, referring to the illustration shown with FIG. 1. Hence, the plane of the leaf 108 will usually extend in the direction of the beam propagation.

The leaf unit 104 is mounted displaceably in an adjusting direction 110. The adjusting direction 110 will usually be oriented perpendicularly with respect to the direction of the radiation beam propagation (not shown). The leaf drive unit 106 is designed to displace the leaf unit 104 linearly in the adjusting direction 110, wherein the leaf drive unit 106 comprises a drive mechanism 112 for displacing the leaf 108 in the adjusting direction 110. According to the invention, said drive mechanism 112 operates based on pneumatic actuation.

In this embodiment, the drive mechanism 112 is particularly suited to displace the leaf unit 104 directed forwards within the adjusting direction 110, i.e. directed to the right side with respect to the illustration shown with FIG. 1, which corresponds to the usual position of a radiation being arranged above the leaf 104, or the usual position of a template, if applicable.

For this purpose, the drive mechanism 112 comprises a pressure cylinder 114. The pressure cylinder 114 generally serves to apply pressure being available or generated within the leaf drive unit 106 directly or indirectly to the leaf unit 104 in order to displace the leaf unit 104 and, simultaneously, the leaf 108 in the adjusting direction 110. In detail, the drive mechanism 112 comprises a piston 116, wherein the piston 116 is linked indirectly to the leaf unit 104, and wherein a displacement of the piston 116 results in a displacement of the leaf unit 104.

It is well visible according to FIG. 1 that the piston 116 is displaceably arranged in the adjusting direction 110 within the pressure cylinder 114. In order to prevent the leakage of gas being applied from the drive mechanism 112 side of the leaf module 102, the piston 116 comprises a sealing element 118, which comprises an o-ring 120 according to this embodiment.

Additionally, according to this embodiment, the drive mechanism 112 comprises a reservoir 122 for compressed gas, wherein the reservoir 122 communicates with the pressure cylinder 114 also being comprised by the drive mechanism 112. The capacity of the reservoir 122 is large compared to the volume of the pressure cylinder 114 in order to attain a flat load deflection curve exhibited by the drive mechanism 112. Also, it is possible to provide one single reservoir 122 supplying compressed gas to several or all drive mechanisms 112 being comprised by at least one side of a multi-leaf collimator (not shown in this figure). The reservoir 122 may for instance be charged with compressed gas using an external or internal (i.e. being arranged within or on the radiotherapy apparatus) hand or foot pump, or an external or internal motor-driven pump (not shown).

The leaf unit 104 as illustrated in FIG. 1 further comprises a guiding rod 124 extending in the adjusting direction 110, wherein the guiding rod 124 is attached to the leaf 108, and wherein the guiding rod 124 is linked to the piston 116 being comprised by the drive mechanism 112. Thus, the leaf unit 104 is linked indirectly to the piston 116 via the guiding rod 124. By being displaceably arranged in the pressure cylinder 114, the guiding rod 124 is also linearly guided by the pressure cylinder 114. Thus, here, the leaf drive unit 106 is designed to displace the leaf unit 104 in the adjusting direction 110 and additionally provide guidance to the leaf unit 104 with respect to any direction being oriented perpendicularly related to the adjusting direction 110.

The leaf 108 may comprise brass for both reduced costs and satisfactory shielding capacity.

Finally, the leaf module 102 according to the embodiment illustrated in FIG. 1 also comprises a second drive mechanism 126 in order to retract the leaf 108 from the radiation beam or the template, if applicable. With other words, said second drive mechanism 126 is adapted to displace the leaf 108 backwards (i.e. directed to the left side according to FIG. 1) within the adjusting direction 110. The second drive mechanism 126 comprises an engagement member 128 extending perpendicularly through a slot hole 130 within the leaf 108. The engagement member 128 may extend through each leaf 108 of an assembly (not shown here) of leaves 108 within a multi-leaf collimator. Thus, by activating the engagement member 128 to move backwards (i.e. to the left side of FIG. 1) all adjacent leaves 108 may simultaneously be retracted from the beam or from the template, if applicable. The second drive mechanism 126, in particular the engagement member 128, may for instance be operated manually, motor-driven, pneumatically as well as the drive mechanism 112, or the like.

It is noted that the term "second drive mechanism" as used herein refers to an optional mechanism 126 to retract the leaf 108 which, compared to the drive mechanism 112 as outlined above does not necessarily, but may operate based on pneumatic actuation.

FIG. 2 illustrates in a predominantly schematic, perspective and partly sectional view a second exemplary embodiment of a leaf module 102 according to the invention, shown with both retracted (top of FIG. 2) and extended (bottom of FIG. 2) leaf unit 104. It is noted that the embodiment of the leaf module 102 according to the invention as shown in FIG. 2 is identical to the embodiment shown in FIG. 1 except for the fact that the embodiment of FIG. 2 is not illustrated with an optional second drive mechanism due to reasons of clarity. Hence, for the explanation of all other features as shown in FIG. 2, full reference is made to the detailed specification given with relation to FIG. 1 in order to avoid repetitions.

From the illustration of FIG. 2, the mode of operation of the drive mechanism 112 according to this embodiment of the leaf module 102 is well comprehensible. For improving clarity, the reservoir 122 and the pressure cylinder 114 are shown in a sectional view. The pressurized gas supplied by the reservoir 122 serves to displace the piston 116 forwards in the adjusting direction 110. The piston 116 is linked indirectly to the leaf 108 via the guiding rod 124 which is attached to the leaf 108. Thus, by displacing the piston 116, the leaf unit 104 and in particular the leaf 108 will be displaced, allowing a precise adjusting of the leaf unit 104.

FIG. 3 illustrates two views of details pertaining to both embodiments of the leaf module 102 according to FIGS. 1 and 2. With other words, said views equally pertain to each embodiment of FIG. 1 and FIG. 2 as these embodiments are identical with respect to the sections shown according to FIG. 3.

In the upper illustration of FIG. 3, a detailed view of the section located in between the reservoir 122 and the leaf 108 is provided. Both reservoir 122 and pressure cylinder 114 are again shown in a sectional illustration. The mode of displacement of the piston 116 within the pressure cylinder 114 is well comprehensible here. Also, it becomes apparent that some substantial linear guidance for the piston 116 and the guiding rod 124 linked thereto is provided by the pressure cylinder 114 when the displacement takes place.

The lower illustration of FIG. 3 shows, in a sectional side view, details of the mounting of the piston 116 and the guiding rod 124 within the pressure cylinder 114. For preventing a leakage of gas being provided from the drive mechanism side, the piston 116 comprises a sealing element 118, i.e. an o-ring 120, snugly fitting the clearance between the piston 116 and the pressure cylinder 114.

FIG. 4 illustrates in a predominantly schematic perspective view an exemplary embodiment of the multi-leaf collimator 132 according to the invention, illustrating the insertion of a template 134 and the adjusting of the collimator 132. The collimator 132 comprises a plurality of leaf modules 102 according to the invention. The embodiment of the leaf modules 102 as shown in the collimator 132 of FIG. 4 is identical with the embodiment as illustrated in FIG. 2, as no optional second drive mechanism is shown here due to reasons of clarity. The multi-leaf collimator 132 according to FIG. 4 comprises two assemblies 136 of leaf modules 102, wherein each assembly 136 comprises a plurality of leaf modules 102 according to the embodiment of FIG. 2, and wherein the leaf modules 102 of each assembly 136 face each other. It is noted that a radiation source (not shown) will usually be arranged above the center line of the collimator 132, i.e. above the template 134.

The adjusting of the collimator 132, i.e. the leaf units 104, with respect to the adjusting direction 110 also becomes apparent from FIG. 4. In the initial position, the leaf units 104 will be retracted from the center line, i.e. the radiation source by a distance being sufficient to allow insertion of the template 134. The initial position may be attained by retracting the leaves 108 with optional second drive mechanisms as outlined above (not shown here). However, the retracting may also be achieved with the drive mechanisms 112, if suitably designed, or manually. After the template 134 has been inserted (as indicated according to FIG. 4) the drive mechanisms 112 will be activated, displacing each leaf 108 forwards in the adjusting direction 110 until abutting with the template 134. Hence, the beam shape for the subsequent irradiation cycle has been established. The template 134 may now remain jammed between the assemblies 136, or it may be removed if suitable means (not shown) for locking the leaves 108 in their adjusting position are available.

It is noted that according to this embodiment, each assembly 136 of leaf modules 102 comprises one single reservoir 122 for compressed gas. Thus, when applying a pressure, each leaf 108 may automatically be subject to one identical force acting in the adjusting direction 110. Thus, a very simple but effective embodiment is attained here. In an alternative, one single reservoir for compressed gas may be provided, corresponding with and simultaneously supplying both assemblies 136. Differing embodiments may however also be designed, with optional valves regulating the gas pressure for each pressure cylinder 114, and/or with different pressure cylinders 114 with varying diameter, thus varying the force being exerted upon a corresponding piston.

The multi-leaf collimator 132 is regarded to be particularly suitable for being employed in Co-60 radiotherapy machines or in mid- and low-end linac apparatuses, but is not restricted thereto. The collimator 132 and the leaf module 102 according to the invention may exhibit a compact design, wherein a simple, reliable and variable adjustability of leaf units 104 is achievable. Said benefits do particularly well match the requirement profile for aforementioned machines, in particular if radiotherapy has to be provided in remote regions, in particular with no or no reliable power network, and/or with insufficiently qualified medical and maintenance staff and/or with limited financial resources.

LIST OF REFERENCE SYMBOLS 102 leaf module
104 leaf unit
106 leaf drive unit
108 leaf
110 adjusting direction (leaf unit)
112 drive mechanism
114 pressure cylinder
116 piston
118 sealing element (piston)
120 o-ring (sealing element)
122 reservoir (for compressed gas)
124 guiding rod
126 second drive mechanism
128 engagement member
130 slot hole
132 multi-leaf collimator
134 template
136 assembly (of leaf modules)

The invention claimed is:
1. A multi-leaf collimator comprising:
a plurality of leaf modules, each leaf module comprising
a leaf unit comprising a leaf for shielding beams from a selected area, the leaf unit being mounted displaceably in an adjusting direction, and
a leaf drive unit configured to displace the leaf of the leaf unit linearly in the adjusting direction, the leaf drive unit comprising at least one drive mechanism that operates based on pneumatic actuation, and
a single reservoir for compressed gas configured to supply compressed gas to several or all drive mechanisms that comprise at least one side of the multi-leaf collimator, wherein the at least one side of the multi-leaf collimator includes more than one leaf module, and wherein the drive mechanism comprises a pressure cylinder.

2. The multi-leaf collimator according to claim 1, wherein the single reservoir communicates with a pressure cylinder being comprised by the drive mechanism.

3. The multi-leaf collimator according to claim 1, wherein the drive mechanism further comprises a piston, wherein the piston is linked directly or indirectly to the leaf unit, and wherein a displacement of the piston results in a displacement of the leaf unit.

4. The multi-leaf collimator according to claim 3, wherein the piston comprises a sealing element.

5. The multi-leaf collimator according to claim 4, wherein the sealing element is an o-ring.

6. The multi-leaf collimator according to claim 1, wherein the leaf unit comprises a guiding rod extending in the adjusting direction, and wherein the guiding rod is a separate part being attached to the leaf.

7. The multi-leaf collimator according to claim 6, wherein the guiding rod is displaceably arranged in a pressure cylinder being comprised by the drive mechanism.

8. The multi-leaf collimator according to claim 7, wherein the pressure cylinder provides a linear guidance to the guiding rod.

9. The multi-leaf collimator according to claim 6, wherein the guiding rod is linked to a piston being comprised by the drive mechanism.

10. The multi-leaf collimator according to claim 1, wherein the leaf drive unit is configured to displace the leaf unit in the adjusting direction and additionally provide guidance to the leaf unit with respect to any direction being oriented perpendicularly related to the adjusting direction.

11. The multi-leaf collimator according to claim 1, wherein the leaf comprises a high density material.

12. The multi-leaf collimator according to claim 11, wherein the high density material is selected from the group consisting of brass, lead and tungsten.

13. The multi-leaf collimator according to claim 1, wherein the multi-leaf collimator comprises two assemblies of leaf modules, wherein the leaf modules of each assembly face each other.

14. The multi-leaf collimator according to claim 13, wherein each assembly of leaf modules comprises one single reservoir for compressed gas.

15. The multi-leaf collimator according to claim 13, wherein the multi-leaf collimator is configured for application in a Cobalt-60 radiotherapy apparatus.

16. The multi-leaf collimator according to claim 13, wherein a single reservoir for compressed gas is provided and configured to correspond with and simultaneously supply the two assemblies of leaf modules.

17. The multi-leaf collimator according to claim 1, wherein the leaf unit comprises a guiding rod extending in the adjusting direction, and wherein the guiding rod is an integral part of the leaf.

18. The multi-leaf collimator according to claim 17, wherein the guiding rod is displaceably arranged in a pressure cylinder being comprised by the drive mechanism.

* * * * *